United States Patent [19]

Shaw

[11] Patent Number: 4,739,063
[45] Date of Patent: Apr. 19, 1988

[54] SELECTIVE HYDROGENATION OF HETEROCYCLIC AROMATIC COMPOUNDS

[75] Inventor: James E. Shaw, Bartlesville, Okla.

[73] Assignee: Phillips Petroleum Company, Bartlesville, Okla.

[21] Appl. No.: 804,576

[22] Filed: Dec. 4, 1985

[51] Int. Cl.$^4$ .................. C07D 215/04; C07D 219/02; C07D 217/02; C07D 209/08

[52] U.S. Cl. ...................................... 546/102; 546/61; 546/101; 546/108; 546/150; 546/166; 546/58; 546/38; 546/33; 548/439; 548/490; 548/420; 548/418; 208/143; 208/254 H

[58] Field of Search ............... 546/101, 102, 108, 150, 546/166, 61; 548/439, 490; 208/143, 254 H

[56] References Cited

U.S. PATENT DOCUMENTS

| | | | |
|---|---|---|---|
| 2,069,662 | 2/1937 | Treppenhauer | 548/490 |
| 3,236,765 | 2/1966 | Erbelding | 208/254 H |
| 3,322,770 | 5/1967 | D'Alessandro et al. | 502/185 |
| 3,383,306 | 5/1968 | Rogers et al. | 208/254 R |
| 3,412,174 | 11/1968 | Kroll | 585/277 |
| 3,444,198 | 5/1969 | Korst | 260/351.5 |
| 3,544,485 | 12/1970 | Taira et al. | 252/477 |
| 3,793,383 | 2/1974 | Johnson et al. | 585/268 |
| 3,929,784 | 12/1975 | Richards | 546/176 |
| 4,372,842 | 2/1983 | Gardner | 208/254 H |
| 4,386,207 | 5/1983 | de Graaf | 546/154 |

OTHER PUBLICATIONS

Ponomarev et al., Khimiya Geterotsiklicheskikh Soedinenii, vol. 2, No. 2, pp. 239–242 (1966).
Nagai et al., Chemical Abstracts, vol. 92, 110338y (1980).
Lynch et al., Chemical Abstracts, vol. 100, No. 17, 138414c (04/23/84).
Fish, Chemical Abstracts, vol. 101, 90107w (1984), abstract of Ann. N.Y. Acad. Sci. 1983, 415, pp. 292–301 (1983).
Fish et al., Chemical Abstracts, vol. 102, 206351y (1985), abstract Electr. Power Res. Inst./Rep.? EPRI AP (Palo Alto, Calif.) 1984 of EPRI AP-3366.
Kirk-Othmer, Encyclopedia of Chemical Technology, 3rd Ed., vol. 19, p. 538.
Heterocyclic Compounds, vol. IV, Elderfield (Ed.) pp. 282–286.
Catal. Rev.–Sci. Eng., 20(2), 155–208 (1979), "Process and Catalyst Needs for Hydrodenitrogenation", J. R. Katzer and R. Sivasubramanian.
Adkins et al., J. Am. Chem. Soc., vol. 63, pp. 1563–1570 (1941).
Cocchetto et al., Ind. Eng. Chem., Process Des. Dev., vol. 15, No. 2, pp. 272–277 (1976).
Aboul-Gheit, Chemical Abstracts, vol. 83, 192155n (1975), vol. 91, 210522b (1979).
Fish et al., J. Am. Chem. Soc., vol. 104, No. 19, pp. 5234–5237 (09/22/82).

*Primary Examiner*—Mark L. Berch
*Assistant Examiner*—Diana G. Rivers
*Attorney, Agent, or Firm*—Hal Brent Woodrow

[57] ABSTRACT

Selective hydrogenation of the unsaturated nitrogen-containing ring in heterocyclic aromatic compounds is promoted by the use of hydrogenation catalysts selected from the group consisting of iridium, iridium dioxide, rhenium, molybdenum oxide, tungsten oxide, chromium trioxide, ferric oxide, iron pentacarbonyl, cobalt oxide-molybdenum oxide and copper chromite.

14 Claims, No Drawings

SELECTIVE HYDROGENATION OF HETEROCYCLIC AROMATIC COMPOUNDS

BACKGROUND OF THE INVENTION

This invention relates to the selective hydrogenation of unsaturated nitrogen-containing rings in heterocyclic aromatic compounds.

Hydrogenation processes resulting in the complete saturation of polynuclear aromatic compounds are well known in the art. For example, naphthalene can be hydrogenated to decalin and quinoline or isoquinoline can be hydrogenated to decahydroquinolines. However, it is also well recognized in the art that selective hydrogenations are difficult to effect on substrates containing a variety of unsaturated sites. Hydrogenation of such materials frequently results in the production of many compositions exhibiting varying degrees of saturation. It follows that the discovery of catalytic hydrogenation systems possessing the capacity for effecting the selective hydrogenation of unsaturated nitrogen-containing rings in heterocyclic aromatic compounds constitutes a significant contribution to the art. Such systems provide practical synthetic routes to useful products as well as possessing the potential to render other processes such as hydrodenitrogenation (HDN) more economical.

In a HDN process, the nitrogen in organic nitrogen compounds is converted to ammonia. This nitrogen must be removed by the process of hydrodenitrogenation (HDN) to prevent poisoning of refining catalysts and to avoid the sale of products which form gums and sediments or cause air pollution on burning. Heavy oil, shale oil and coal-derived liquids contain high levels of such nitrogenous compositions. If the feedstream to a HDN process contains homocyclic aromatics as well as heterocyclic aromatic compounds characterized by the presence of unsaturated nitrogen-containing rings, significant amounts of hydrogen can be consumed by the undesirable hydrogenation of the homocyclic aromatics. This undesired nonselective hydrogenation reaction increases the overall cost of the process because hydrogen is expensive. Current HDN methods consume more hydrogen than necessary to remove nitrogen as ammonia because in a typical hydrodenitrogenation process homocyclic aromatic rings are hydrogenated. Thus, HDN processes based on more selective hydrogenation catalysts need to be developed and would be highly preferred.

One value of the instant selective hydrogenation process resides in its potential use as the initial step of a hydrodenitrogenation operation. The application of the instant process as the front end of a HDN operation would result in hydrogenation of the unsaturated nitrogen containing rings in the heterocyclic aromatic compositions without promoting hydrogenation of the homocyclic aromatics. This would result in lower process costs because less hydrogen would be consumed. The second step of the HDN process involving hydrogenolysis of C-N bonds to complete the removal of nitrogen as ammonia would be effected by other chemical means.

THE INVENTION

In accordance with the present invention, I have discovered that heterocyclic aromatic compounds characterized by the presence of unsaturated nitrogen-containing rings are selectively hydrogenated in the heterocyclic ring by contacting the heterocyclic aromatic compound with at least one hydrogenation catalyst under hydrogenation conditions wherein the catalyst is selected from the group consisting of iridium, rhenium, tungsten oxide, molybdenum oxide, iridium dioxide, chromium trioxide, ferric oxide, iron pentacarbonyl, cobalt oxide-molybdenum oxide and copper chromite or mixtures thereof.

The heterocyclic aromatic compounds which can be selectively hydrogenated in the nitrogen-containing ring are those of the formulas I, II, III and IV:

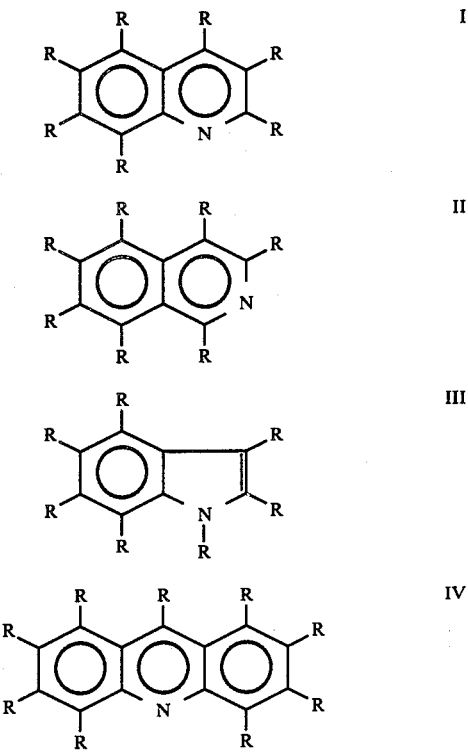

wherein R represents hydrogen, alkyl groups containing 1 to 20 carbon atoms and adjacent R groups can be divalent 1,4-(alkadienyl-1,3) radicals with the proviso that the total number of carbon atoms in the compound does not exceed 40.

Representative heterocyclic aromatic compounds include quinoline, isoquinoline, indole, 2-methylquinoline, acridine, carbazole, 4-methylquinoline; 2,4-dimethylquinoline; 2-isobutylquinoline and phenanthridine.

Other materials suitable for use in the present invention include heavy oil, shale oil and coal-derived liquids which contain the disclosed heterocyclic aromatic compounds or derivatives thereof.

If desired, the invention can be carried out in the presence of a solvent. Representative solvents suitable for use in the present invention include paraffins containing preferably five to sixteen carbon atoms such as pentane, cyclohexane, hexane, heptane, octane, decane, dodecane and hexadecane. Suitable aromatic solvents include benzene, toluene and xylenes. It is noteworthy that aromatic solvents such as toluene undergo no aromatic ring hydrogenation in the instant process. No methylcyclohexane or methylcyclohexene was detectable by gas liquid chromatographic analysis in hydrogenations carried out in toluene solvent.

In practicing the instant invention, the temperature varies over the broad range of 25° to 300° C., preferably over the range of 100° to 250° C. The initial pressure of the reaction system is adjusted into the broad range of atmospheric to 3000 psi (gauge), preferably over the range of 500 to 2000 psi. The time of reaction varies over the broad range of 0.1 hour to 10 hours with a preferred range of 1 to 4 hours. It is recognized, of course, that the necessary reaction time will depend on the temperature, hydrogen pressure and catalyst concentration.

The following Examples I–VIII illustrate the present invention. Example IX is a representative control run. Invention runs are summarized in Table I.

EXAMPLE I

Hydrogenation of 2-Methylquinoline with Re/Al$_2$O$_3$

To a 300 mL autoclave was added 10.0 g (0.070 mol) 2-methylquinoline, 90.0 g n-hexadecane and 0.20 g Re/Al$_2$O$_3$ (5 weight percent rhenium). The autoclave was flushed with H$_2$ four times and then pressured to 800 psi with hydrogen at room temperature. The autoclave was heated with rapid stirring to 170° C. over a period of 0.5 hour and then maintained at 170° C. for 3.5 hours. The highest pressure at 170° C. was 1030 psi and the final pressure was 690 psi.

The autoclave was cooled and the contents were suction filtered. Gas liquid chromatographic analysis of the colorless liquid filtrate on a 6'×⅛" 10% Carbowax 20M column at 200° C. showed that the only product of the reaction was 2-methyl-1,2,3,4-tetrahydroquinoline (96% 2-methyl-1,2,3,4-tetrahydroquinoline and 4% starting material). There were no detectable amounts of 2-methyl-5,6,7,8-tetrahydroquinoline and 2-methyldecahydroquinoline. Gas liquid chromatographic analysis with an external standard showed that the absolute yield of product based on consumed starting material was 100%. The use of cyclohexane as the solvent instead of n-hexadecane gave the same result (97% of 2-methyl-1,2,3,4-tetrahydroquinoline and 3% of 2-methylquinoline).

An additional hydrogenation run was carried out as described above except for the inclusion of an equimolar amount of naphthalene in the n-hexadecane solvent system. It was noteworthy that none of the naphthalene was hydrogenated to tetralin or decalin and 2-methylquinoline was hydrogenated exclusively to 2-methyl-1,2,3,4-tetrahydroquinoline. This shows that not only is the benzenoid aromatic ring in 2-methylquinoline not hydrogenated but the benzenoid aromatic rings in other compounds present are not hydrogenated.

EXAMPLE II

Hydrogenation of 2-Methylquinoline with Ir/C

A 300 mL autoclave containing 10.0 g (0.070 mol) 2-methylquinoline, 90 g n-hexadecane and 0.2 g of 5% iridium on carbon was pressured with hydrogen to 700 psi, stirred briefly and then the pressure was released. This was repeated four more times. The autoclave was then pressured with hydrogen to 780 psi. The autoclave was heated with rapid stirring at 132° C. for 2.5 hours. The autoclave was cooled and the contents were suction filtered. Gas liquid chromatographic analysis of the colorless liquid filtrate on a 6'×⅛" 10% Carbowax 20M column at 200° C. showed that the only product of the reaction was 2-methyl-1,2,3,4-tetrahydroquinoline (97% 2-methyl-1,2,3,4-tetrahydroquinoline and 3% starting material). There was no 2-methyl-5,6,7,8-tetrahydroquinoline or 2-methyldecahydroquinoline. Gas liquid chromatographic analysis with an external standard showed that the absolute yield of product based on consumed starting material was 99%.

EXAMPLE III

Hydrogenation of 2-Methylquinoline with Fe(CO)$_5$

A 300 mL autoclave containing 10.0 g 2-methylquinoline, 90.0 g n-hexadecane and 0.6 mL iron pentacarbonyl was pressured with hydrogen to 700 psi, stirred briefly and then the pressure was released. This was repeated four more times. The autoclave was pressured with hydrogen to 780 psi and then heated with rapid stirring at 250° C. for 7.5 hours.

The autoclave was cooled and the contents were suction filtered. Gas liquid chromatographic analysis of the colorless filtrate on a 6'×⅛" 10% Carbowax 20M column at 200° C. showed that the only product of the reaction was 2-methyl-1,2,3,4-tetrahydroquinoline (69% 2-methyl-1,2,3,4-tetrahydroquinoline and 31% starting material).

EXAMPLE IV

Hydrogenation of 2-Methylquinoline with Fe$_2$O$_3$/Al$_2$O$_3$

A 300 mL autoclave containing 10 g (0.07 mol) 2-methylquinoline, 90 g n-hexadecane and 1.0 g Fe$_2$O$_3$ on alumina was pressured to 700 psi with hydrogen, stirred briefly and then the pressure was released. This was repeated four more times. The autoclave was pressured with hydrogen to 800 psi, heated with rapid stirring to 290° C. over 3.5 hours and then maintained at 300° C. for an additional four hours.

The autoclave was cooled and the contents were suction filtered. Gas liquid chromatographic analysis of the colorless filtrate on a 6'×⅛" 10% Carbowax column at 200° C. showed that the only product of the reaction was 2-methyl-1,2,3,4-tetrahydroquinoline (81% 2-methyl-1,2,3,4-tetrahydroquinoline and 19% starting material).

EXAMPLE V

Hydrogenation of 4-Methylquinoline with Ir/Al$_2$O$_3$

A 300 mL autoclave containing 7.5 g 4-methylquinoline, 67.5 g n-hexadecane and 0.3 g of 5% iridium on alumina was pressured to 500 psi with hydrogen, stirred briefly and then the pressure was released. This was repeated three more times. The autoclave was pressured to 750 psi with hydrogen, heated with rapid stirring to 160° C. and maintained at 160° C. for 4.5 hours.

The autoclave was cooled and the contents were suction filtered. Gas liquid chromatographic analysis of the colorless filtrate on a 6'×⅛" 10% Carbowax 20M column at 180° C. showed that the only product of the reaction was 4-methyl-1,2,3,4-tetrahydroquinoline (97% 4-methyl-1,2,3,4-tetrahydroquinoline and 3% starting material).

EXAMPLE VI

Hydrogenation of 2-Methylquinoline with IrO$_2$

A 300 mL autoclave containing 7.5 g 2-methylquinoline, 67.5 g n-hexadecane and 0.3 g iridium dioxide was pressured to 500 psi with hydrogen, stirred briefly and then the pressure was released. This was repeated three more times. The autoclave was pressured with hydrogen to 750 psi, heated with rapid stirring to 150° C. and then maintained at 150° C. for 7 hours.

The autoclave was cooled and the contents were suction filtered. Gas liquid chromatographed analysis of the colorless filtrate on a 6'×⅛" 10% Carbowax 20M column at 180° C. showed that the only product of the reaction was 2-methyl-1,2,3,4-tetrahydroquinoline (94% 2-methyl-1,2,3,4-tetrahydroquinoline and 6% 2-methylquinoline).

EXAMPLE VII

Hydrogenation of 2-Isobutylquinoline with Re/Al$_2$O$_3$

A 300 mL autoclave containing 7.5 g 2-isobutylquinoline, 67.5 g n-hexadecane and 0.2 g of 5% rhenium on alumina was pressured to 500 psi with hydrogen, stirred briefly and then the pressure was released. This was repeated three more times. The autoclave was pressured to 750 psi with hydrogen, heated with rapid stirring to 200° C. and then maintained at 200° C. for 7 hours.

The autoclave was cooled and the contents were suction filtered. Gas liquid chromatographic analysis of the colorless filtrate on a 6'×⅛" 10% Carbowax 20M column at 200° C. showed that the only product was 2-isobutyl-1,2,3,4-tetrahydroquinoline (94% 2-isobutyl-1,2,3,4-tetrahydroquinoline and 6% 2-isobutylquinoline).

the control Pt/Al$_2$O$_3$ catalyst (run 13) system promoted hydrogenation in both the benzenoid aromatic ring and the nitrogen heterocyclic ring.

Run 14 in Table I demonstrates the selective hydrogenation capacity of the Re/Al$_2$O$_3$ catalyst on a substrate of 2-isobutylquinoline. In this run, none of the 5,6,7,8-tetrahydroquinoline isomer was detectable in the gas liquid chromatograhic analysis.

The most active of the instant catalyst systems was the iridium-on-carbon system (run 3). This selective hydrogenation system provided the 1,2,3,4-tetrahydro derivative (exclusively) at a reaction temperature of 132° C. The least active instant catalyst system was the Fe$_2$O$_3$/Al$_2$O$_3$ system which provided the 1,2,3,4-tetrahydro derivative at a reaction temperature of 300° C.

EXAMPLE VIII

This example describes the selective hydrogenation of indole with the inventive Re/Al$_2$O$_3$ catalyst system.

A 300 mL autoclave containing 10 g indole, 90 g n-hexadecane and 0.6 g of 5% rhenium on alumina was pressured to 700 psi with hydrogen, stirred briefly and then the pressure was released. This was repeated four more times. The autoclave was pressured to 1815 psi, heated with rapid stirring to 227° C. and then maintained at 227° C. for 7 hours. The highest hydrogen

TABLE I

| | | | | | Reaction | | |
|---|---|---|---|---|---|---|---|
| | Run | Catalyst[b] | Type of | Temp. | Time | Product Ratio[d] | |
| Quinoline* | No. | (Wt. g) | Run | °C. | Hr.[c] | % 1,2,3,4-Tetrahydro | % 5,6,7,8 Tetrahydro |

Selective Hydrogenation of Nitrogen-Heterocyclic Rings in Quinolines[a]

| Quinoline* | Run No. | Catalyst[b] (Wt. g) | Type of Run | Temp. °C. | Reaction Time Hr.[c] | % 1,2,3,4-Tetrahydro | % 5,6,7,8 Tetrahydro |
|---|---|---|---|---|---|---|---|
| 2-MQ | 1 | Pd/Al$_2$O$_3$(0.2) | Control | 160 | 1.0 | 54 | 46 |
| 2-MQ | 2 | Re/Al$_2$O$_3$(0.2) | Invention | 170 | 3.5 | 100[e] | 0 |
| 2-MQ | 3 | Ir/C(0.3) | Invention | 132 | 2.5 | 100[e] | 0 |
| 2-MQ | 4 | IrO$_2$(0.3) | Invention | 150 | 7 | 100 | 0 |
| 2-MQ | 5 | MoO$_3$/Al$_2$O$_3$(0.7) | Invention | 250 | 5 | 100[e] | 0 |
| 2-MQ | 6 | WO$_3$/Al$_2$O$_3$(0.7) | Invention | 250 | 3.5 | 100[e] | 0 |
| 2-MQ | 7 | Cr$_2$O$_3$/Al$_2$O$_3$(0.7) | Invention | 250 | 3.5 | 100[e] | 0 |
| 2-MQ | 8 | Fe$_2$O$_3$/Al$_2$O$_3$(1.0) | Invention | 300 | 7 | 100[f] | 0 |
| 2-MQ# | 9 | CoO—MoO$_3$/Al$_2$O$_3$ | Invention | 250 | 3 | 100 | 0 |
| 2-MQ# | 10 | Copper Chromite | Invention | 200 | 3 | 100 | 0 |
| 2-MQ | 11 | Fe(CO)$_5$(0.9) | Invention | 250 | 7.5 | 100[f] | 0 |
| 4-MQ | 12 | Ir/Al$_2$O$_3$(0.3) | Invention | 160 | 4.5 | 100 | 0 |
| 4-MQ | 13 | Pt/Al$_2$O$_3$(0.2) | Control | 160 | 2 | 97 | 3 |
| 2-IBQ | 14 | Re/Al$_2$O$_3$(0.2) | Invention | 200 | 7 | 100 | 0 |

[a]Initial hydrogen pressure was 750 psi at room temperature.
[b]The supported catalysts contained 5 wt % Re, 5 Wt % Ir, 10 Wt % MoO$_3$, 10 Wt % WO$_3$, 15 Wt % Cr$_2$O$_3$ and 20 Wt % Fe$_2$O$_3$. The CoO—MoO$_3$/Al$_2$O$_3$ (Shell 344) contained 9.6 Wt % Mo (as MoO$_3$) and 2.4 Wt % Co (as CoO); copper chromite analyzed 51 Wt % CuO and 47 Wt % Cr$_2$O$_3$. In run 11, Fe(CO)$_5$ was added as the neat liquid.
[c]To estimate total reaction time 0.5 hour required to reach the desired temperature should be added to each entry.
[d]Unless otherwise noted, no other products were detectable by gas liquid chromatographic analysis except for 2–3% starting material.
[e]Absolute yield was 99–100% based on consumed starting material.
[f]Unreacted starting material was 20–30%.
*2-MQ, 4-MQ and 2-IBQ represent, respectively, 2-methylquinoline, 4-methylquinoline and 2-isobutylquinoline.
In these runs 0.7 g of catalyst was used.

Referring to invention runs 2–11 in Table I, it is evident that the instant catalysts, respectively, Re/Al$_2$O$_3$; Ir/C; IrO$_2$; MoO$_3$/Al$_2$O$_3$; WO$_3$/Al$_2$O$_3$; Cr$_2$O$_3$/Al$_2$O$_3$; Fe$_2$O$_3$/Al$_2$O$_3$; CoO-MoO$_3$/Al$_2$O$_3$; copper chromite; and Fe(CO)$_5$ were effective for the exclusive hydrogenation of the nitrogen-containing heterocyclic ring in 2-methylquinoline whereas the control Pd/Al$_2$O$_3$ catalyst (run 1) system resulted in reduction of both the benzenoid aromatic ring (leading to the production of 5,6,7,8-tetrahydro isomer) and the nitrogen-heterocycle ring (leading to the production of the 1,2,3,4-tetrahydro isomer).

Referring to runs 12 and 13 in Table I, it is evident that the Ir/Al$_2$O$_3$ catalyst system (run 12) was effective for the exclusive hydrogenation of the nitrogen-containing heterocyclic ring in 4-methylquinoline whereas pressure at 227° C. was 2610 psi and the final pressure was 2510 psi.

After cooling the autoclave to ambient temperature, the contents were suction filtered. Gas liquid chromatographic analysis of the colorless filtrate on a 1.5'×⅛" 10% Carbowax 20M column at 150° C. showed that the product mixture contained 80% indoline and 20% indole.

A series of control runs, e.g., Example IX, was carried out in a 300 mL stainless steel autoclave to determine the extent to which the benzenoid aromatic ring and the nitrogen-containing heterocyclic ring in alkyl-substituted quinolines undergo hydrogenation with conventional catalysts. The results of these runs are summarized in Table II.

TABLE II

Hydrogenation* of Alkyl-substituted Quinolines Over Conventional Catalysts

| Feedstock[a] | Catalyst[b] | Run No. | Temp °C. | Reaction Time Hr.[c] | % Distribution of Products[d] | |
|---|---|---|---|---|---|---|
| | | | | | 1,2,3,4-Tetrahydro | 5,6,7,8-Tetrahydro |
| 2-MQ | Pd/Al$_2$O$_3$ | 1 | 160 | 1.0 | 54 | 46 |
| 2-MQ | Pt/Al$_2$O$_3$ | 2 | 150 | 1.0 | 92[e] | 8 |
| 2-MQ | Pt/C | 3 | 150 | 1.0 | 96[e] | 4 |
| 2-MQ | Ru/Al$_2$O$_3$ | 4 | 160 | 1.6 | 74 | 26[f] |
| 2-MQ | Rh/Al$_2$O$_3$ | 5 | 100 | 0.5 | 63 | 37 |
| 2-MQ | Ni/SiO$_2$—Al$_2$O$_3$ | 6 | 160 | 1.5 | 74 | 26 |
| 2-MQ | Raney Ni | 7 | 160 | 2.2 | 63 | 37 |
| 2-MQ | NiO—MoO$_3$/Al$_2$O$_3$ | 8 | 300 | 3.0 | 92[g] | 8[h] |
| 4-MQ | Pt/Al$_2$O$_3$ | 9 | 160 | 2.0 | 97 | 3 |
| 4-MQ | Ni/SiO$_2$—Al$_2$O$_3$ | 10 | 160 | 1.5 | 64 | 36 |
| 6-MQ | Pd/Al$_2$O$_3$ | 11 | 105 | 1.0 | 98.5 | 1.5 |
| 2,4-DMQ | Pt/Al$_2$O$_3$ | 12 | 160 | 1.5 | 88 | 12 |

*Initial hydrogen pressure was 750 psi (gauge) at room temperature.
[a]2-MQ; 4-MQ; 6-MQ and 2,4-DMQ represent, respectively, 2-methylquinoline; 4-methylquinoline; 6-methylquinoline and 2,4-dimethylquinoline.
[b]Catalysts were 5% metal except for Ni/SiO$_2$—Al$_2$O$_3$ which was 60 to 65% Ni and Ni—Mo/Al$_2$O$_3$ which was 2.4% Ni (as NiO) and 11.6% Mo (as MoO$_3$).
[c]To estimate total reaction time 0.5 hour required to reach the desired temperature should be added to each entry.
[d]Unless otherwise noted, no other products were detectable except for 2–3% starting material.
[e]Absolute yield was 100% based on consumed starting material.
[f]Decahydroquinoline was detectable (12%).
[g]In this run, 6-7% starting material was unreacted.
[h]At 250° C. the ratio of the 1,2,3,4-tetrahydro derivative to the 5,6,7,8-tetrahydro derivative was 99:1.

Referring to the control runs in Table II, it is evident that none of these hydrogenation systems yielded 100% of the 1,2,3,4-tetrahydro derivatives to the exclusion of the 5,6,7,8-tetrahydro derivatives.

EXAMPLE IX

Hydrogenation of 2-Methylquinoline with Pt/Al$_2$O$_3$

To a 300 mL autoclave was added 10.0 g (0.070 mol) of 2-methylquinoline, 90.0 g n-hexadecane and 0.2 g of 5% platinum on alumina. The autoclave was pressured with hydrogen to 700 psi, the contents were stirred briefly and then pressure was released. This was repeated three more times. The autoclave was then pressured with hydrogen to 750 psi at ambient temperature and then heated with rapid stirring (1100 rpm) to 150° C. over a period of 0.5 hour and thereafter maintained at 150° C. for one hour.

The autoclave was cooled to room temperature and the contents were suction filtered. To obtain complete recovery, the autoclave and catalyst were flushed with acetone and this solution was stripped to a residual liquid which was combined with the primary filtrate. Gas liquid chromatography/mass spectral analysis showed that the reaction product consisted of 90% 2-methyl-1,2,3,4-tetrahydroquinoline, 8% 2-methyl-5,6,7,8-tetrahydroquinoline and 2% 2-methylquinoline (starting material). The ratio of the 1,2,3,4-tetrahydro derivative to the 5,6,7,8-tetrahydro derivative was 92:8 (see run 2 in Table II). The 2-methyl-1,2,3,4-tetrahydroquinoline was identified by comparison with an authentic sample (infrared, nuclear magnetic resonance and mass spectral analyses). The 2-methyl-5,6,7,8-tetrahydroquinoline material was verified by similar analyses giving:

IR(neat 1594, 1573, 808 cm$^{-1}$; NMR(CDCl$_3$) δ 1.58–2.18 (m, 4H), 2.51 (s, 3H), 2.53–3.20 (m, 4H); 6.87, 7.27 (ABq, 2H, J=HZ); MS m/e 147 (M+).

Anal. Calcd. for C$_{10}$H$_{13}$N: C, 81.58; H, 8.90; N, 9.52. Found: C, 81.32; H, 8.98; N, 9.43.

Reasonable variations and modifications are possible within the scope of the disclosure and the appended claims to the invention.

That which is claimed is:

1. A process for the selective hydrogenation of the nitrogen-containing ring in at least one heterocyclic aromatic compound of the formulas I, II, III and IV

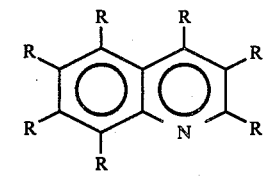

I

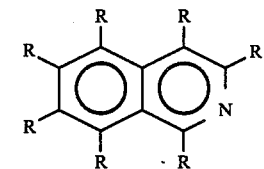

II

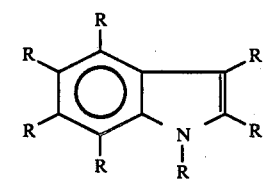

III

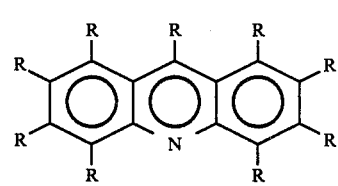

IV wherein R represents hydrogen, alkyl groups containing 1 to 20 carbon atoms and adjacent R groups can be divalent 1,4-(alkadienyl-1,3) radicals with the proviso that the total number of carbon atoms in the heterocyclic aromatic compound does not exceed 40 which comprises contacting said heterocyclic aromatic compound with hydrogen under hydrogenation conditions at a temperature within the range of 25° C.–300° C. in the presence of at least one hydrogenation catalyst selected from the group consisting of iridium, iridium dioxide, rhenium, tungsten oxide, and ferric oxide.

2. A process in accordance with claim 1 wherein said process is carried out at a hydrogen pressure in the range of atmospheric to 3000 psi.

3. A process in accordance with claim 1 wherein the heterocyclic aromatic compound is selected from the group consisting of quinoline, isoquinoline, indole, phenanthridine, 2-methylquinoline, acridine, carbazole, 4-methylquinoline; 6-methylquinoline, 2,4-dimethylquinoline and 2-isobutylquinoline.

4. A process in accordance with claim 1 wherein said heterocyclic aromatic compound is 2-methylquinoline and said hydrogenation catalyst is rhenium on alumina.

5. A process in accordance with claim 1 wherein said heterocyclic aromatic compound is 2-methylquinoline and said hydrogenation catalyst is iridium on carbon.

6. A process in accordance with claim 1 wherein said heterocyclic aromatic compound is 2-methylquinoline and said hydrogenation catalyst is iridium dioxide.

7. A process in accordance with claim 1 wherein said heterocyclic aromatic compound is 2-methylquinoline and said hydrogenation catalyst is tungsten oxide on alumina.

8. A process in accordance with claim 1 wherein said hetero-cyclic aromatic compound is 2-methylquinoline and said hydrogenation catalyst is chromium trioxide on alumina.

9. A process in accordance with claim 1 wherein said heterocyclic aromatic compound is 2-methylquinoline and said hydrogenation catalyst is ferric oxide on alumina.

10. A process in accordance with claim 1 wherein said heterocyclic aromatic compound is 4-methylquinoline and said hydrogenation catalyst is iridium on alumina.

11. A process in accordance with claim 1 wherein said heterocyclic aromatic compound is 2-isobutylquinoline and said hydrogenation catalyst is rhenium on alumina.

12. A process in accordance with claim 1 wherein said heterocyclic aromatic compound is indole and said hydrogenation catalyst is rhenium on alumina.

13. A process in accordance with claim 1 wherein said selective hydrogenation of the nitrogen-containing ring in said heterocyclic aromatic compound is carried out in a solvent selected from the group consisting of pentane, cyclohexane, hexane, heptane, octane, decane, dodecane, hexadecane, benzene, toluene and xylenes.

14. A process in accordance with claim 1 wherein said heterocyclic aromatic compounds are components present in heavy oil, shale oil and coal-derived liquids.

* * * * *

UNITED STATES PATENT AND TRADEMARK OFFICE
CERTIFICATE OF CORRECTION

PATENT NO. : 4,739,063

DATED : April 19, 1988

INVENTOR(S) : James E. Shaw

It is certified that error appears in the above-identified patent and that said Letters Patent is hereby corrected as shown below:

Col. 9, line 2, after "tungsten oxide," please insert ---chromium trioxide,---.

Signed and Sealed this

Twentieth Day of September, 1988

Attest:

DONALD J. QUIGG

Attesting Officer

Commissioner of Patents and Trademarks